US006918896B2

(12) United States Patent
McMurdo (10) Patent No.: US 6,918,896 B2
(45) Date of Patent: Jul. 19, 2005

(54) USER POWERED PERSONAL HYGIENE APPARATUS

(76) Inventor: John B. McMurdo, 140 San Marin Dr., Novato, CA (US) 94945

( * ) Notice: Subject to any disclaimer, the term of this patent is extended or adjusted under 35 U.S.C. 154(b) by 0 days.

(21) Appl. No.: 10/351,084

(22) Filed: Jan. 24, 2003

(65) Prior Publication Data

US 2003/0220620 A1 Nov. 27, 2003

Related U.S. Application Data (63) Continuation of application No. 08/766,325, filed on Dec. 13, 1996, now abandoned.

(51) Int. Cl.$^7$ .............................................. A61M 31/00
(52) U.S. Cl. ..................................... 604/279; 604/295
(58) Field of Search ........................ 604/19, 27, 36–37, 604/48, 514–517, 73, 181, 185, 187, 212, 257, 264, 275, 279, 290, 310; 222/206, 212, 478–479, 481–482, 213, 566, 568, 572; 215/40, 42, 44, 370–373, 376, 900, 378–385, 902, DIG. 3

(56) References Cited

U.S. PATENT DOCUMENTS

| | | | |
|---|---|---|---|
| 1,666,197 A | | 4/1928 | Dolmatch |
| 1,903,681 A | * | 4/1933 | Merliss ........................ 604/181 |
| 3,948,105 A | | 4/1976 | Johnson, Jr. |
| 4,140,120 A | | 2/1979 | Yamauchi |
| 4,259,954 A | | 4/1981 | Scott |
| 4,292,846 A | | 10/1981 | Barnett |
| 4,324,242 A | | 4/1982 | Cross |
| 4,405,321 A | | 9/1983 | Budoff |
| 4,622,704 A | | 11/1986 | Chung |
| 5,097,539 A | | 3/1992 | Tchorbadjian |
| 5,097,540 A | | 3/1992 | Lovitt |
| 5,226,574 A | * | 7/1993 | Durinzi, Jr. .............. 222/465.1 |
| 5,271,104 A | | 12/1993 | LaTora |
| 5,331,692 A | | 7/1994 | Alberti |
| 5,361,427 A | | 11/1994 | Wilk |
| 5,447,110 A | | 9/1995 | Brown |

* cited by examiner

Primary Examiner—Nicholas D. Lucchesi
Assistant Examiner—Michael M Thompson
(74) Attorney, Agent, or Firm—Dorsey & Whitney; Robert B. Chickering; Victor E. Johnson (57) ABSTRACT

A self contained, user powered, portable bidet apparatus to facilitate and provide cleansing action with versatility, comfort and convenience. An ergonomically designed vessel (20) with a discharge nozzle (22) and nozzle tip (24) attached and angled (FIG. 6A) so as to vigorously discharge a cleansing stream of fluid when the vessel (20) is filled with fluid, inverted, pivoted into position under the anus or genital area and user compressed with hand pressure. Easy to fill with a wide range of solutions, and solution temperatures, lightweight, aesthetically pleasing, unbreakable, and versatile the apparatus can incorporate detachable nozzle tips (26) allowing the user to customize water pressure and flow characteristics.

9 Claims, 13 Drawing Sheets

USER POWERED PERSONAL HYGIENE APPARATUS

This a continuation of application Ser. No. 08/766,325, filed Dec. 13, 1996, now abandoned.

BACKGROUND

1. Field of Invention

This invention relates to the field of personal hygiene specifically external cleansing of the anus, the surrounding folds of the anus and the external genital regions of human beings.

2. Background—Description of Prior Art

The problem of personal hygiene is shared by all human beings. Toilet paper as a quick and convenient means of cleaning up has major drawbacks such as incomplete cleaning that leaves residues that cause discomfort, irritation, and in some cases can lead to infection. Soap and water showers and baths address the need and desire for cleanliness, however, a bath or shower is not always convenient or available. Devices have been devised and invented to address the need for a quick and thorough clean-up. The classic bidet works well and is ideal for this purpose, however, not many people have bidets available, and, a bidet is not portable. Apparatus designed for attachment to existing toilets and utilizing plumbing and hoses and a water supply to achieve their results are workable, however, these devices are not portable and seem out of place, cumbersome and possibly contaminated. Examples of such apparatus are described in Tchorbadjian, U.S. Pat. No. 5,097,539 (1990), LaTora, U.S. Pat. No. 5,271,104 (1992), Alberti, U.S. Pat. No. 5,331,692 (1993), Wilk, U.S. Pat. No. 5,361,427 (1994). Several portable washing devices exist apparently to address the lack of portability of fixed-in-place washing devices. One device referenced Chung, U.S. Pat. No. 4,622,704 (1984) is portable but extremely bulky and needs electricity in order to power its water supply. Yamauchi, U.S. Pat. No. 4,140,120 (1979) addressed the problem of portability, however, this device seems to be limited to internal vaginal cleaning and is designed for insertion. Lovitt, U.S. Pat. No. 5,097,540 (1992) has addressed the portability problem, however, this device is battery operated and has moving mechanical parts to electrically pump the wash solutions.

OBJECTS AND ADVANTAGES

The object of providing warn and cold wash water for personal cleansing has been approached in many different ways, and every apparatus has its own particular method of achieving the end result. The objective and purpose of the USER POWERED PERSONAL HYGIENE APPARATUS (UPPHA) is to achieve a superior result with superior convenience, simplicity, economy, and true portability. My UPPHA achieves this performance superiority through its geometry, ergonomic design and the resulting function. My UPPHA utilizes and incorporates an integrated group of materials and devices as follows: a flexible plastic hand-compressible and re-expanding vessel shaped to fit comfortably within the inner thigh and crotch area, a neck and nozzle extends from the vessel and is precisely angled so that a short forward rotation of the vessel on a pivot point positions a nozzle-tip directly beneath the anus while a person is either sitting on the toilet or squatting. The vessel is filled by means of an opening located at the base of the vessel which is then sealed with a cap that also incorporates a valve that may be opened and closed easily to allow for the introduction of air to re-expand the vessel, thus, providing the unit with more volume to compress and thereby maintaining a means for continuous high water pressures and cleaning effectiveness. This feature allows the user to easily control the amount of pressure desired by varying the degree of hand pressure.

Since no plumbing is required the user has a wide range of choices for the solutions to be introduced and expelled when using the UPPHA Water temperature can be controlled and vary from cold to warm. The introduction of cleansing agents or soaps may be added if desired. Two units may be used should the user want to wash with a soapy solution and rinse with clear clean water or antiseptic rinse.

Different nozzle-tips can be attached and detached. Different nozzle tips have qualities and wash characteristics ranging from soft to high pressure water jets, thus, allowing the user to select the wash that is most effective. Squeezing the vessel provides the energy to expel the solution. The degree of pressure depends on the force of the squeeze and the nozzle tip hole size. Because of the unique geometry, when pivoting the apparatus the nozzle tip easily rotates away from the application area and the unit form-fits comfortably in the thigh area while the user wipes or readies for another application of solution. Because the tip rotates away from the anus, chances for contaminating the unit are minimal, however, the unit is easily washed and disinfected and because of the changeable nozzle-tips multiple users can use the device without fear that the tip has been contaminated.

My UPPHA is ergonomic, attractive and quick and easy to set up and use. Only a water source is needed. There are no cords, batteries, expensive plumbing or fixtures. The UPPHA is lightweight and self contained. The UPPHA can be used by campers, mothers with small children, hospital care workers, and anyone that desires superior hygiene and comfort. It reduces the need for extensive wiping and the resulting irritation and debris that are left behind. My UPPHA quickly and conveniently gives a person the means to "freshen up" without having to shower or bathe. Since the UPPHA is inexpensive to manufacture, it is easy to acquire. Besides the preceding there are many other important advantages to using my UPPHA. Less toilet paper is needed, paper resources are conserved and a monetary saving occurs for the user. Many people will opt to use the UPPHA instead of taking a full shower, thus, saving water resources. People with hemorrhoids or infected, swollen anal tissues will find this method exactly what they need to properly care for themselves.

Further objects and advantages of the UPPHA will become apparent from a consideration of the drawings and ensuing description.

In the drawings, closely related figures have the same number but different alphabetic suffixes.

FIG. 2A shows a one piece molded-together-connecting-cap, nozzle and connection tip for a removable-nozzle-tip, while

REFERENCE NUMERALS IN DRAWINGS 12 base-of-vessel filling-point-cap
14 base-of-vessel
16 air-valve
18 filling-point cap-connection
20 tapering-vessel-body connection for
21 tapering-vessel-body with
22 molded-to-vessel discharge-neck discharge-neck
23 vessel with discharge-neck connection (shown with front fill point)
24 molded-in-place discharge-nozzle-tip
25 discharge hole(s)
26 detachable-nozzle-tip connection
28 detachable-nozzle-tip
30 molded-in semi-flexible transition connection
32 vessel discharge-neck
34 connecting-cap for vessel discharge-neck-connection
36 seal
37 kidney-shaped base end vessel
38 kidney-shaped-base (shown with molded-in vessel-discharge-neck and detachable-nozzle-tip)
39 molded-in oval-perimeter-shaped-neck
40 kidney-shaped-vessel (shown with arched molded-in discharge neck and detachable nozzle tip)
41 separate vessel-discharge-neck
44 one piece (molded to connecting cap) discharge-neck
45 connecting-cap (molded to discharge-neck)
46 vessel sealing-cap-for-travel
47 vessel without bottom-fill-cap or air-valve
48 vessel side profile
49 triangular-discharge-neck-perimeter (top view)
50 phantom position
51 center-axis
52 oval-discharge-neck perimeter(top view)
53 application-point
54 side view of triangular discharge-neck-perimeter
55 axis-of-rotation

DETAILED DESCRIPTION

Figure 1A:
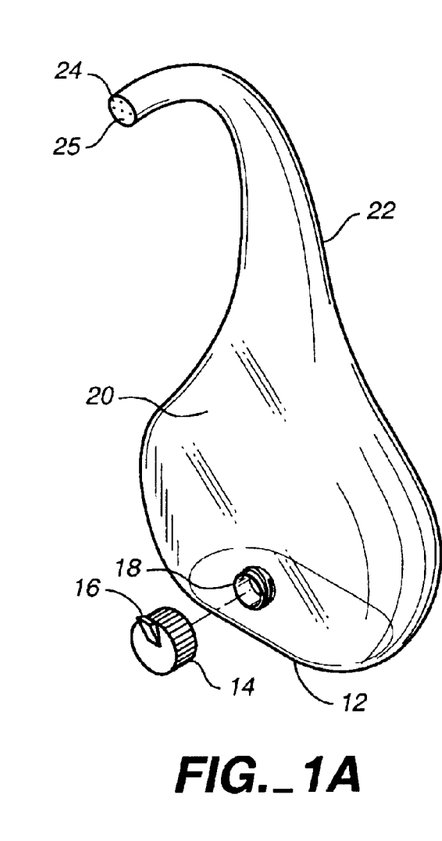
FIGS. 1A to 1I show various embodiments of the User Powered Personal Hygiene Apparatus (UPPHA) with their different aspects, appearances, parts and variations.

A typical embodiment of the User Powered Personal Hygiene Apparatus (UPPHA) is illustrated in FIG. 1A which is an angled view showing both front and partial side views of the unit and exploded view of detachable parts. My UPPHA has a base 12 that provides static stability for the unit when placed in the shown upright position. Base 12 consists of an appropriate plastic material with enough thickness to ensure rigidity and enough base area to ensure a good degree of stability when the unit is filled or empty. The appropriate plastic material will have properties that will resist heat, breakage, chemicals, and have the ability to withstand repeated flexing and compression and return to shape without fracturing; such as, but not limited to, LDPE (Low density polyethylene). Above base 12 is filling-point for the vessel body 20 consisting of a filling-point-cap 14 with an integral-air-valve 16 and a connection point 18 on the vessel-body 20 near the bottom of the tapering-vessel-body 20. The tapering-vessel-body 20 typically is designed to contain from 500 ml to 1500 ml of fluid depending on the model size. Fill-cap 14 and integral air valve consists of strong plastic material such as nylon, polypropylene or other suitable material and molded so as to provide a positive seal between the fill cap 14 and the connection 18 on the vessel body. Air-valve 16 consists of a rotating ball type valve that lets air in when pulled into the upward position and lays flat when closed. The base 12 material is typically 2.5 to 3.5 mm in thickness and the cap connection 18 is molded to a similar thickness where it joins the vessel body 20 providing rigidity. Upward from base 12 is the tapering vessel body 20 which is made of the same flexible plastic as the base and typically 1 mm to 2 mm in thickness for flexibility. The tapering-vessel body 20 is triangular in shape and designed to narrow on a gradient from base 12 to molded-to-vessel discharge-neck 22. Molded to vessel discharge neck 22 narrows on a gradient uniformly to, typically, a one inch diameter and is shaped with either a round, triangular, or oval shaped interior channel and/or similarly shaped exterior perimeter. Tapering vessel body 20 and molded-to vessel discharge neck 22 is shaped to conform to the thigh area of a person while sitting on a toilet. Base 12 typically is 3.5 inches by 7 inches or a 2 to one ratio length to width. Smaller capacity units will of course have smaller dimensions but similar shapes and features. The tapering vessel body 20 narrows on a gradient to the approximately 1 inch diameter vessel discharge neck 22 ending at the molded in place discharge nozzle tip 24. Molded to vessel discharge neck 22 is arcuate so as to typically curve and extend outward to a point typically aligned with the front edge of the base 12 or somewhat beyond and downward so as to be typically one inch below the highest point of the curve or arch of the discharge neck 22.

The molded-to-discharge-neck 22 is typically thicker and more rigid than the vessel body 20 as it is not designed to be compressed. At the end point of the discharge-neck is a nozzle-tip 24 consisting of discharge hole(s) 25. Nozzle tip 24 is angled so as to provide an upward discharge of fluid when the unit is inverted for use, typically 40 to 60 degrees, so that a forward rotation of the vessel body 20 pivots and rotates the discharge nozzle tip 24 and discharge hole(s) directly beneath the anus, see FIG. 6A. In FIG. 1A discharge nozzle tip 24 and discharge hole(s) are molded together.

Figure 1B:
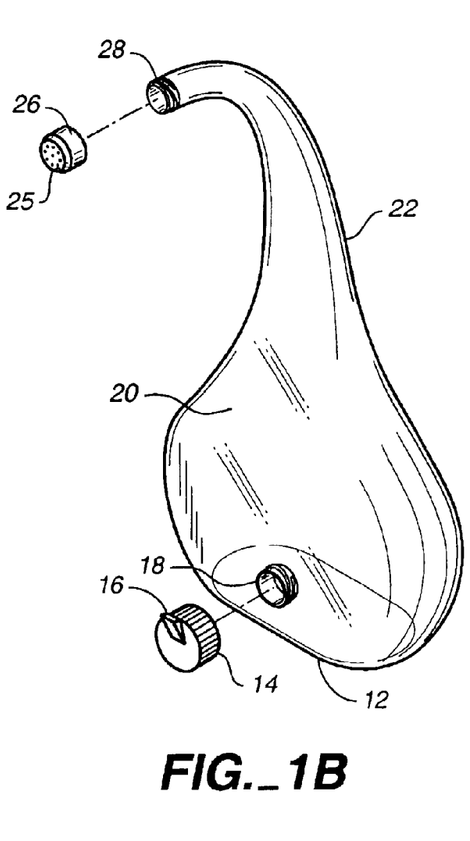

FIG. 1B illustrates another similar embodiment that shares all of the features of FIG. 1A except this embodiment incorporates a detachable-nozzle-tip 26 with discharge hole(s) molded into the tip and the tip is attachable and detachable to the molded-to-vessel discharge-neck 22 at the detachable-nozzle-tip-connection 28. A nozzle-tip with no discharge hole(s) (not shown) can be used to completely seal the vessel so that it may be transported filled without spilling contents.

Figure 1C:
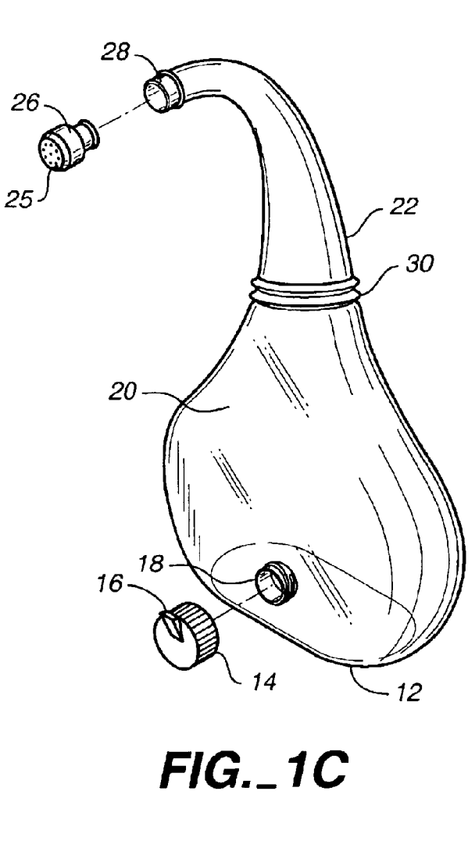

FIG. 1C is a similar embodiment sharing the features of FIGS. 1A and 1B but incorporates a molded-in semi-flexible transition that allows some movement of the molded-to-vessel discharge-neck 22

Figure 1D:
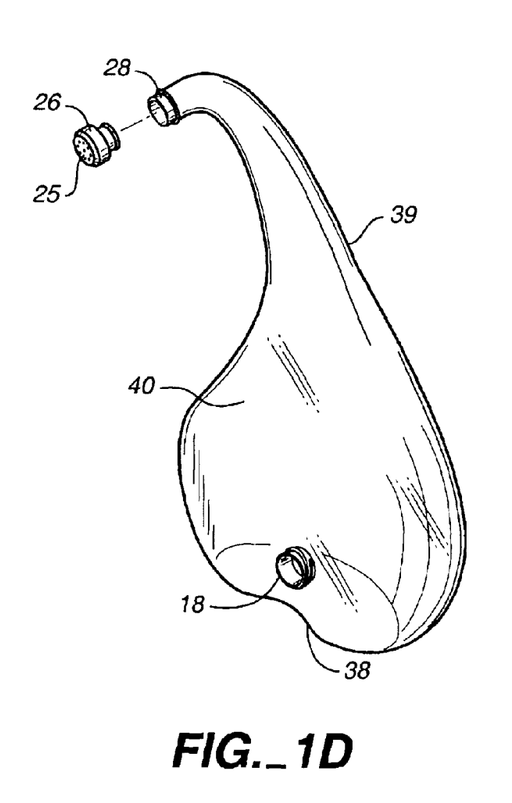

FIG. 1D is another similar embodiment sharing the features of FIGS. 1A and 1B but shown without the base-of-vessel filling-cap 14 and air-valve 16 the differences of this embodiment include a kidney-shaped-vessel 40 and base 38 and a recessed filling-cap-connection 18 that fits in the middle of the kidney shaped curve. FIG. 1D also shows a molded-in oval-perimeter-shaped neck 39 that curves forward on a gradient.

Figure 1E:
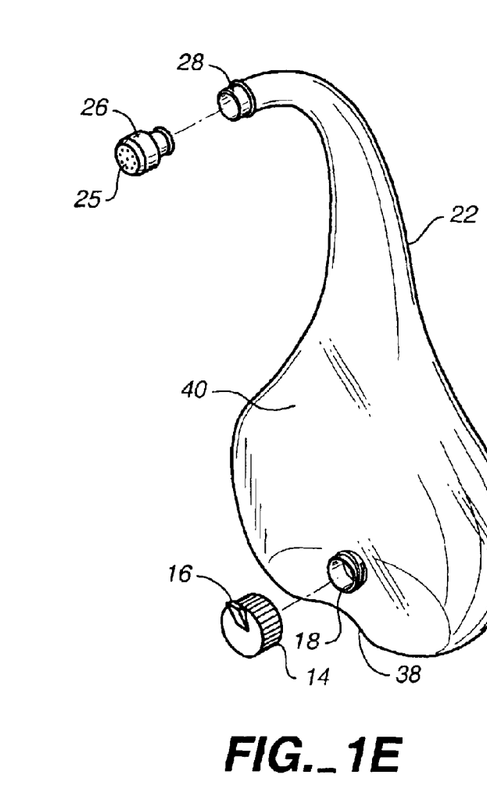

FIG. 1E is a similar embodiment of FIG. 1D and shows all the features of FIGS. 1A and 1B as well. This embodiment has a straighter molded-to vessel discharge-neck 22 as compared to FIG. 1D and has a greater degree of arch rather than a gradient curve.

Figure 1F:
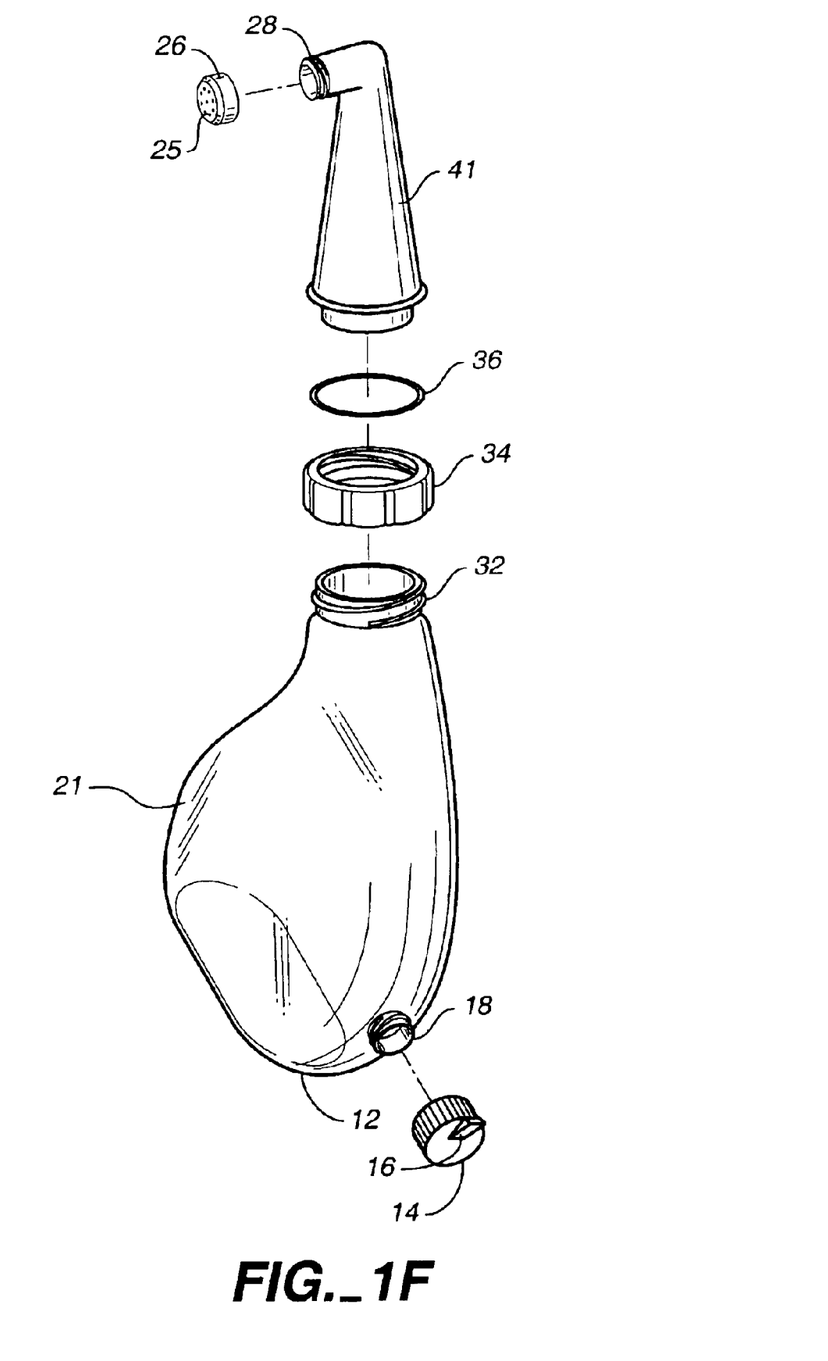

FIG. 1F is an exploded view of another embodiment that shares the features and functions of the previous FIGS. 1A to 1E but is made with an attachable separate discharge neck 41, a tapering-vessel-body-with-connection-for-discharge-neck (shown with side fill point) 21, a seal 36, and a connecting-cap for vessel-discharge-neck-connection 32.

Figure 1G:
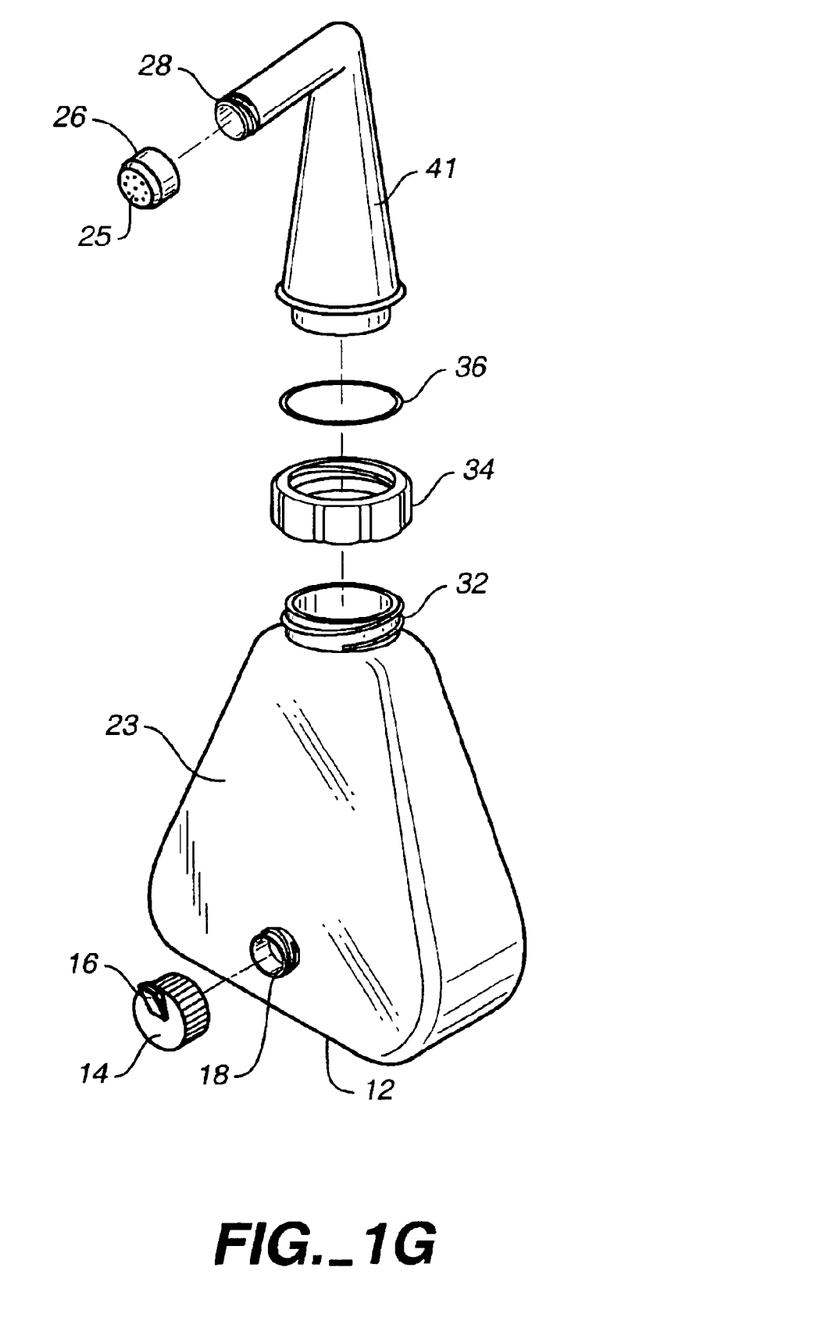

FIG. 1G is a similar embodiment as FIG. 1F pictured with a vessel with discharge-neck connection (shown with front-fill-point) 32 and the vessel 23 having more pronounced angular lines and triangular shape.

Figure 1H:
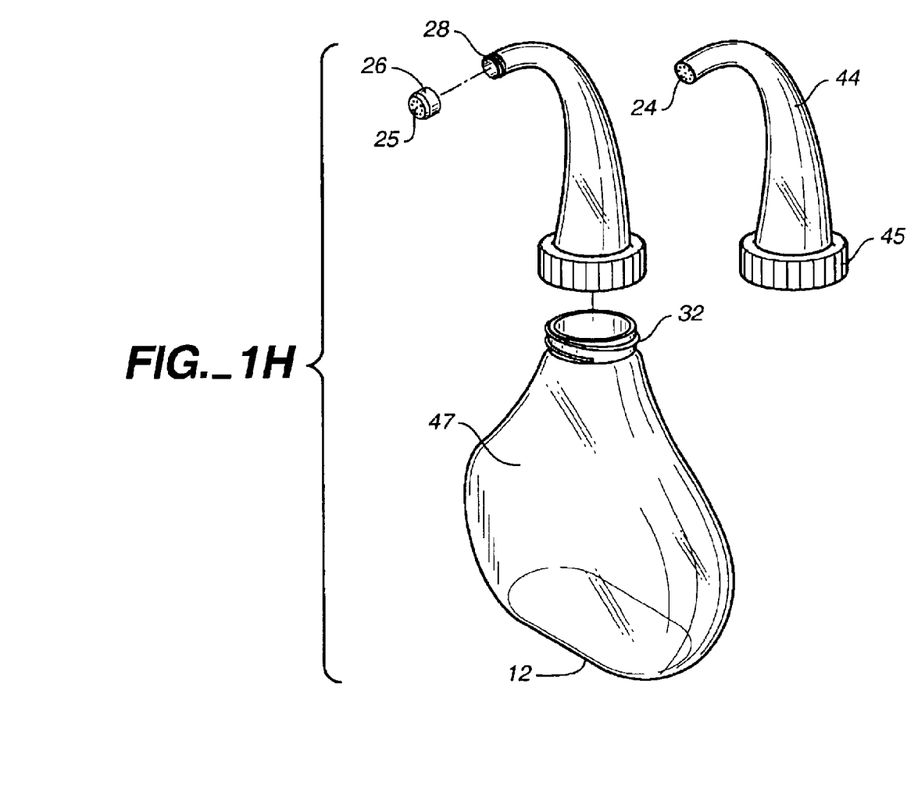

FIG. 1H is an embodiment incorporating a vessel-without-a-bottom-fill-cap 47, two versions of a one-piece (molded to connecting cap) discharge-neck 44 with connecting-cap 45. One version shown with molded-in-place-discharge-nozzle 24 and the other version shown with detachable-nozzle-tip 26 and detachable-nozzle-tip-connection 28. Filling is accomplished by detaching connecting-cap 45, or, with the version shown with detachable-nozzle-tip 26, filling can be accomplished through the connection point by detaching the nozzle-tip 26. Detachable nozzle-tips 26, connecting-caps 45 and fill-caps are manufactured with positive leak proof bottle sealing technology. Materials are high grade injection molded and/or blow molded thermoplastic.

Figure 1I:
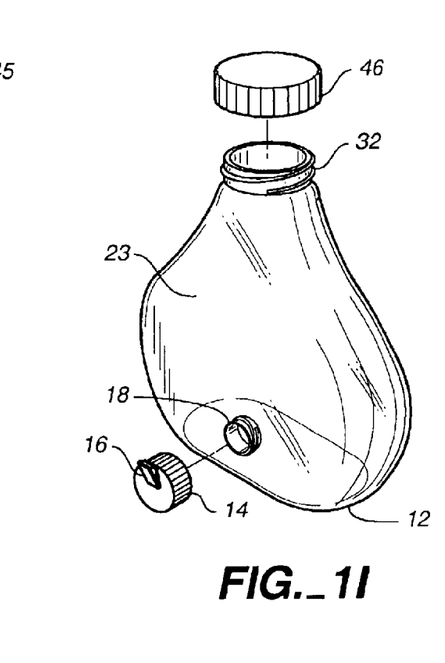

FIG. 1I shows a vessel similar to the one in FIG. 1H. This figure shows the vessel with discharge-neck-connection 32 (shown with front fill point), filling-point-cap-connection 18, base-of-vessel-filling-point-cap 14 and air-valve 16. FIG. 1I also shows a vessel-sealing-cap 46 for travel, used to carry a filled vessel without spilling contents. The base-of-vessel-filling-point-cap 14 with the air-valve 16 is a preferred embodiment since it makes filling convenient and easy and facilitates re-expansion of vessel.

Figure 2A:
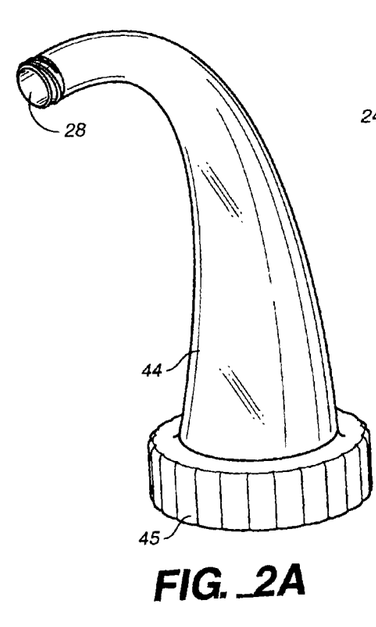
Figure 2B:
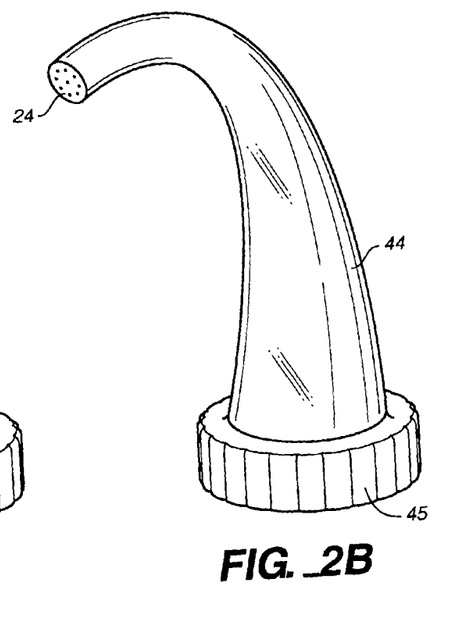
FIG. 2B shows the same piece but with a molded-in discharge-nozzle.

FIGS. 2A and 2B show the one piece (molded to connecting cap' discharge neck 44 and the two versions are identical except for the nozzle tip. FIG. 2A illustrates a detachable nozzle tip connection 28 which allows for variety of detachable nozzle tips. FIG. 2B shows the molded in place discharge nozzle.

Figure 2C:
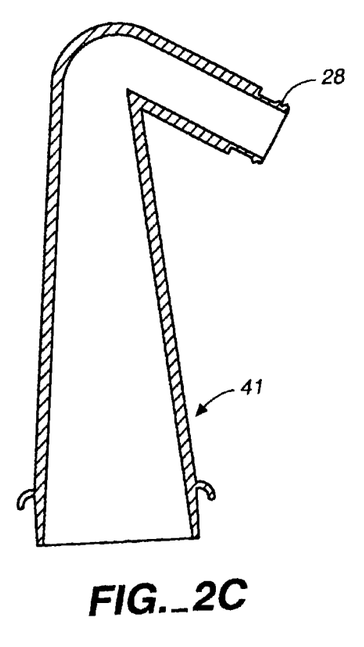
FIGS. 2C and 2D show item 38 in FIG. 1G and is a nozzle representation that illustrates the angled offset of the discharge neck and nozzle tip and the circular perimeter geometry of the nozzle neck.
Figure 2D:
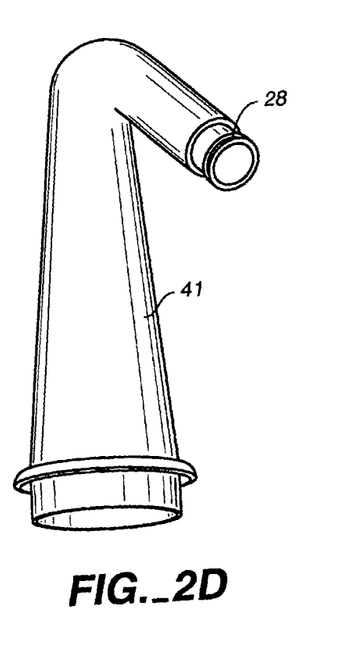
Figure 3A:
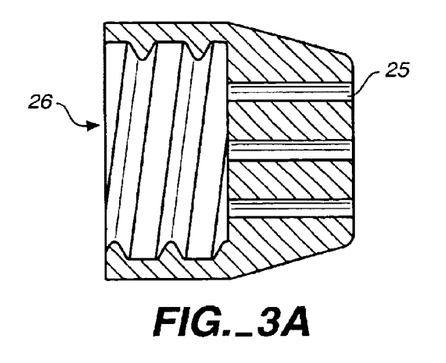
FIGS. 3A to 3F show cut-away of various nozzle-tip designs illustrating discharge channels and exit points.
Figure 3B:
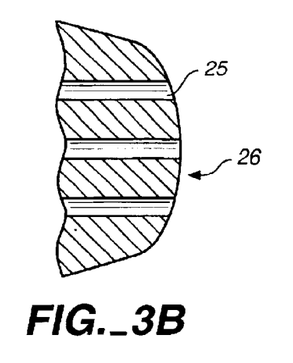
Figure 3C:
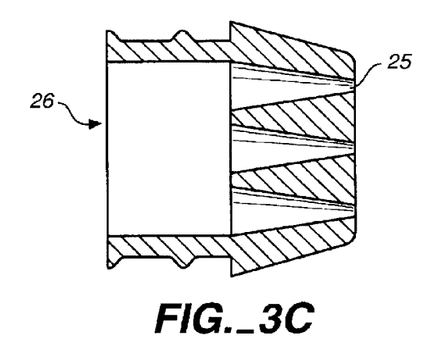
Figure 3D:
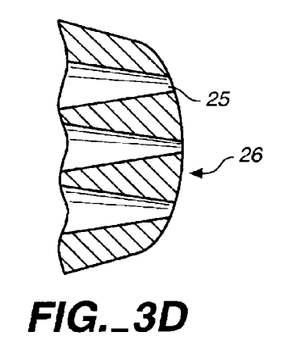
Figure 3E:
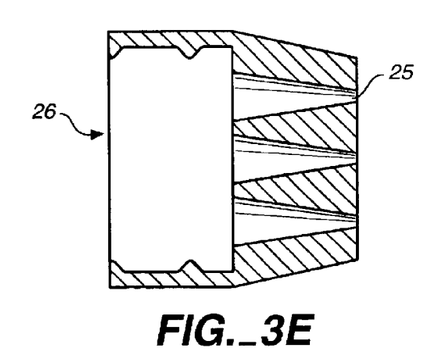
Figure 3F:
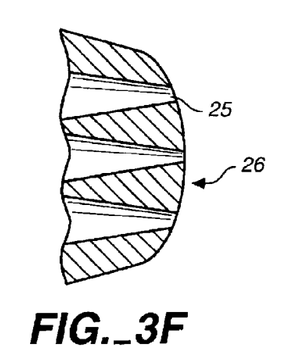
Figure 4A:
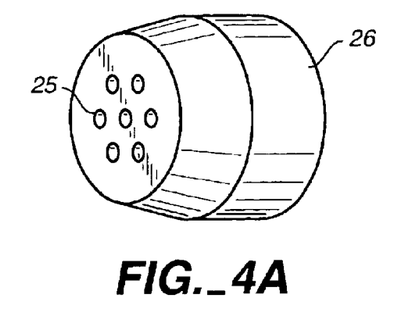
FIGS. 4A to 4F illustrate the detachable nozzle tip with several variations and shows the feature of varying numbers of discharge holes.
Figure 4B:
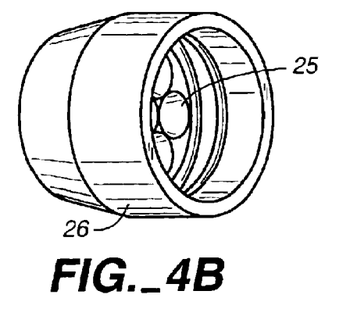
Figure 4C:
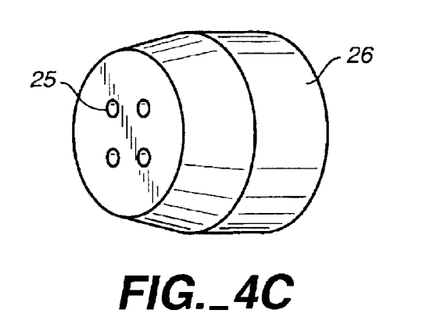
Figure 4D:
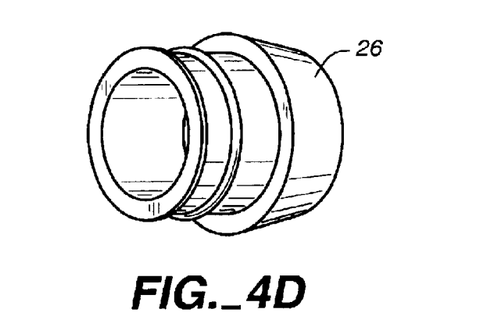
Figure 4E:
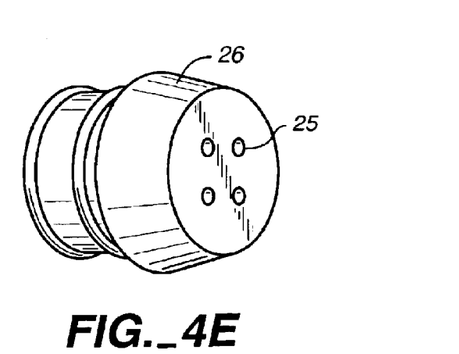
Figure 4F:
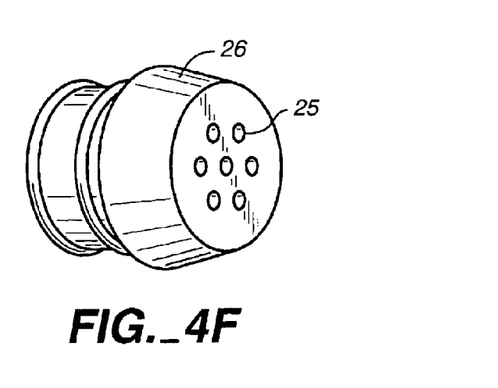

FIGS. 2C and 2D show another detachable type discharge neck previously shown in the exploded view in FIG. 1G item 41. FIG. 2C illustrates the piece 41 and FIG. 2D is a cut-away view of the piece showing the general angles and geometry.

FIGS. 3A to 3F show various cut away views of detachable nozzle tip 26. A nozzle tip typically will have a means for attachment to the vessel discharge neck. And have molded in discharge hole(s). In some embodiments precise cone shaped channels may be molded in as shown in FIGS. 3C,3D,3E and 3F. These tips can be manufactured using injection or blow molding technology. High strength thermoplastic resins will be used to mold tips and tints may be added to impart colors to the items. Preferred materials are polyethylene, polypropylene, nylon, vinyl, or any plastic material that is strong, unbreakable, will accept pigmentation is not affected by soaps, is chemical resistant and can be heated to a temperature sufficient to sterilize. Cut away views are shown with tips that have flat end discharge points and rounded discharge points.

FIGS. 4A to 4F show exterior views of the detachable nozzle tip 26 and show that tips are attachable, detachable and can have different hole(s) arrangements and size. (Typically 1 to 8 hole(s) 0.5 mm to 3 mm in diameter).

Figure 5A:
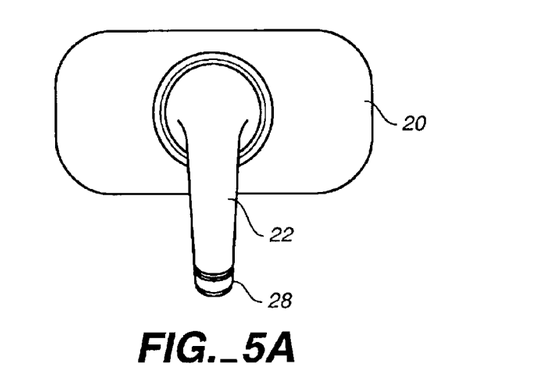
FIGS. 5A to 5C show a front, side, and top view of FIG. 1C to illustrate the nozzle tip offset and the angled nature of the discharge point in relation to the center vertical axis of the vessel body.
Figure 5B:
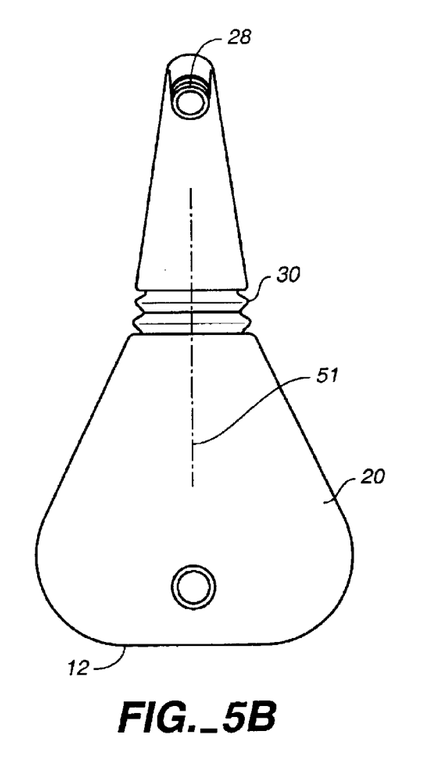
Figure 5C:
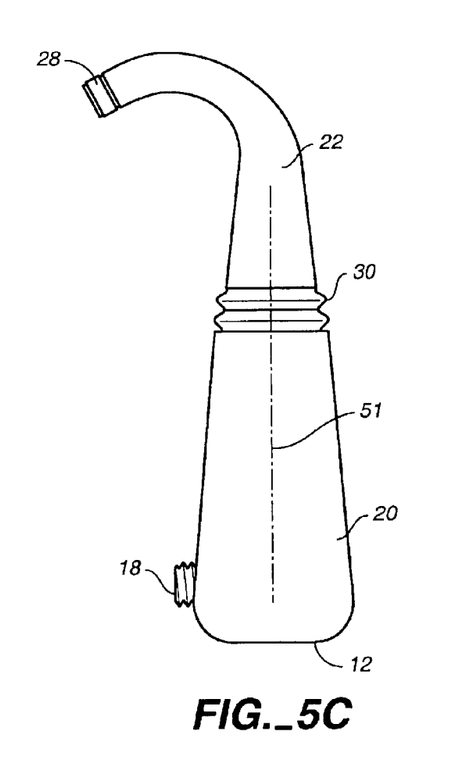

FIGS. 5A to 5C show a top view, side view and front view of one embodiment in order to illustrate the angle on the discharge neck and the angle of the nozzle tip. FIG. 5A, top view, shows the discharge neck 22 extending away from the tapering vessel body 20.

FIG. 5B shows the nozzle tip 26 in relation to the vessel 22 and the discharge neck 20. FIG. 5C shows the center axis 51 and the angle of the discharge nozzle tip so that discharge is upward at typically a 45 degree angle away from the center axis when vessel is inverted for use.

Figures 6A, 7A:
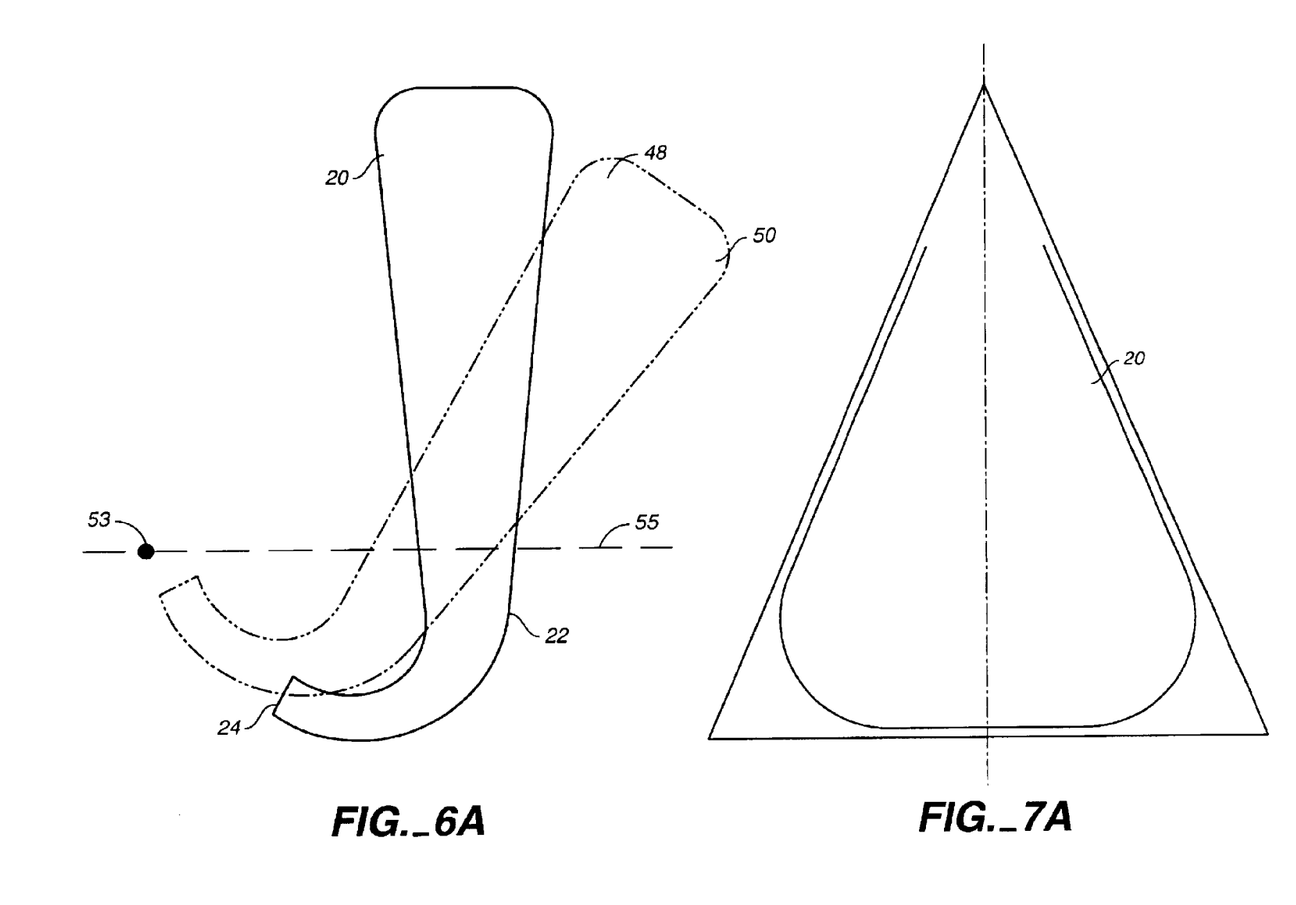
FIG. 6A shows how a short forward rotation will position the apparatus for use.
FIG. 7A illustrates the triangular nature of the vessel body (wide base tapering body).

FIG. 6A shows a basic profile shape of the invention inverted 48 and positioned above and below an axis-of-rotation 55 and in front of an application-point 53 which would be the anus. The phantom position 50 illustrates how the discharge neck 22 and the nozzle tip 24 pivots at, and rotates clockwise beneath, the axis-of rotation 55 toward a position directly under the application point when the vessel-body 48 is moved clockwise above the axis-of-rotation 55. A reverse motion moves the nozzle tip 24 and the discharge neck 22 away from the application-point 53.

FIG. 7A illustrates the triangular nature of the tapering-vessel-body 20.

Figure 8A:
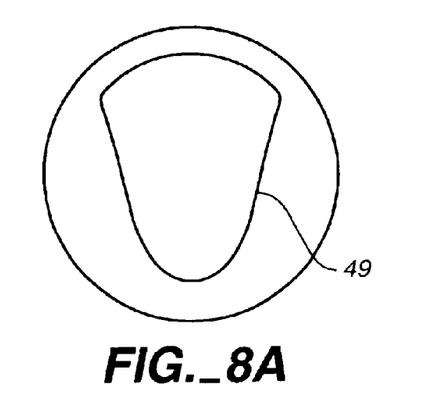
FIGS. 8A to 8C show a nozzle neck perimeter geometry that is not circular and shows an oval and triangular perimeter geometry.

FIG. 8A illustrates a triangular-discharge-neck-perimeter 49.

Figure 8B:
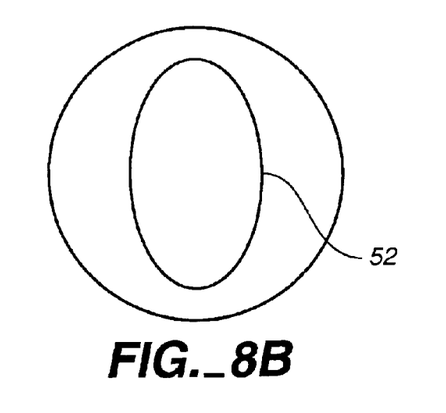
Figure 8C:
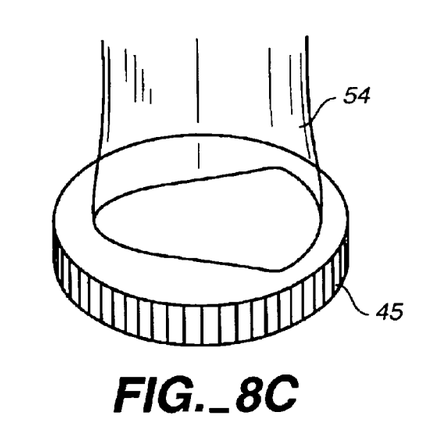
Figure 9A:
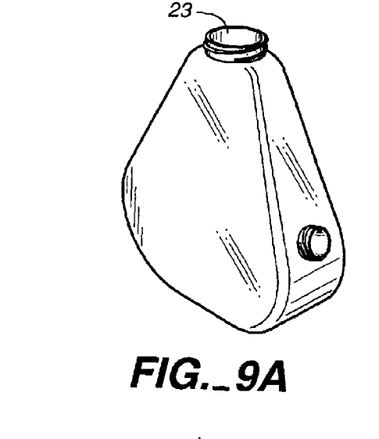
FIGS. 9A and 9F show some vessel body shapes with a cut-away.
Figure 9B:
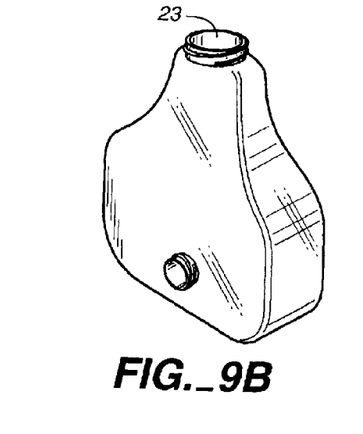
Figure 9C:
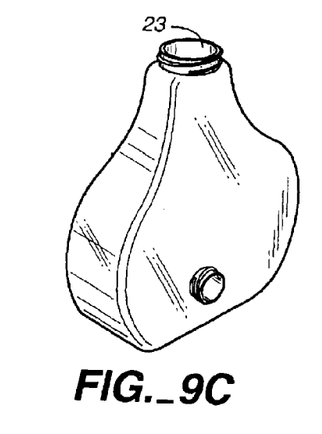
Figure 9D:
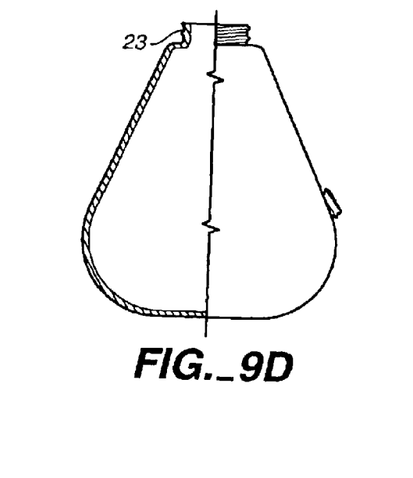
Figure 9E:
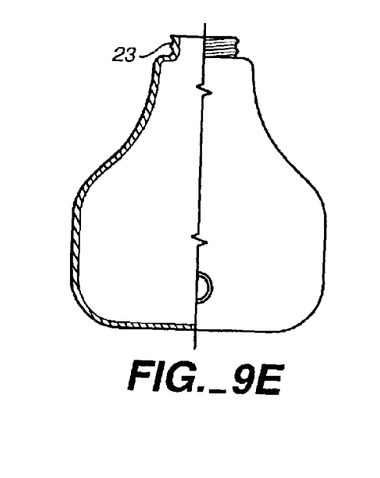
Figure 9F:
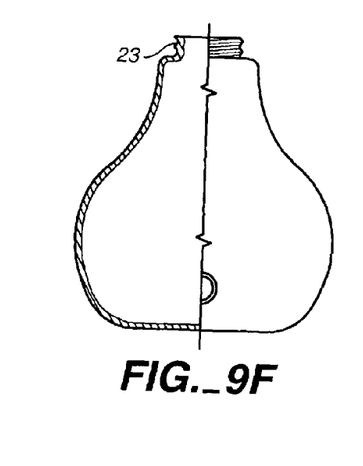

FIG. 8B illustrates an oval discharge-neck-perimeter 52. FIG. 8C illustrates a side view of a triangular discharge-neck perimeter 54.

FIGS. 9A to 9F illustrate several triangular shaped vessels with discharge-neck-connections 93.

Figure 10A:
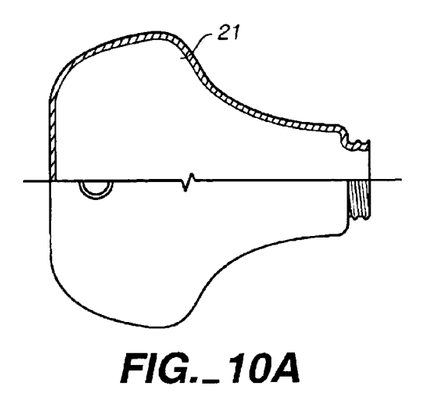
FIGS. 10A to 10C show a vessel body with an oval-shaped base, front view with cut-away, bottom and side views.

FIG. 10A illustrates the tapering-vessel-body 21 with filling-point-cap-connection 18 with cutaway front view.

Figure 10B:
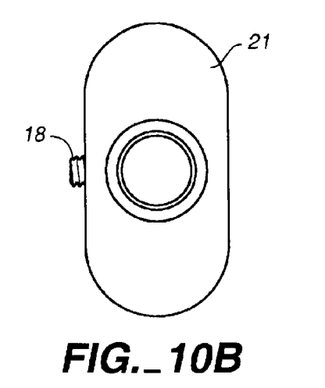

FIG. 10B illustrates the oval base of the vessel-body 21.

Figure 10C:
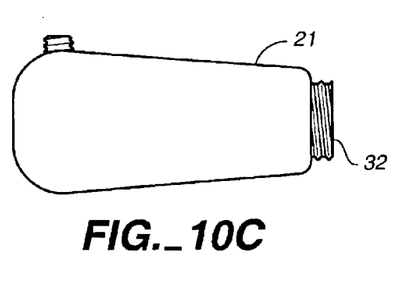

FIG. 10C illustrates the tapering-vessel-body 21 side view.

Figure 11A:
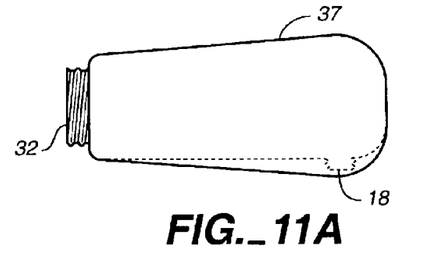
FIGS. 11A to 11C show a vessel with the kidney-shaped base and body, side view, bottom view and front view with cut-away.

FIG. 11A illustrates the side view of the kidney-shaped base and vessel 37 with broken lines indicating the recessed position of the filling-point-cap-connection 18.

Figure 11B:
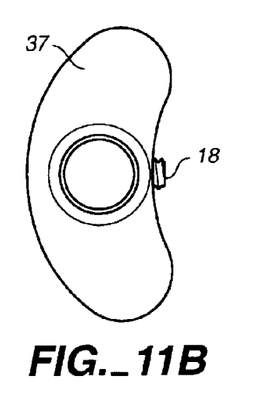

FIG. 11B illustrates a bottom view of a kidney-shaped-base and vessel 37 and shows the recessed filling-point-cap-connection 18. Note: This shaped vessel and base is a preferred embodiment.

Figure 11C:
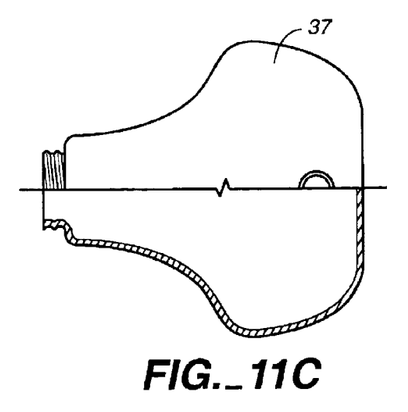

FIG. 11C is a front view of kidney-shaped-base and vessel 37 to illustrate the triangular vessel shape.

Note: All components of the User Powered Personal Hygiene Apparatus can be manufactured from the class of materials in the category of thermoplastic resins and include all ethylene resins, nylon resins, vinyl, and polypropylene. The shapes required can be produced through the use of blow and injection molding technology. Rubber may be used as a material though it is not a preferred material. Pigments to add color to the products can be used. Molds with designs, lettering, ridges, textured gripping surfaces or any other adornments may be included without altering the utility of the overall product. Dimensions of my UPPHA can vary in proportion to the intended users, adults or children. In general the base-of-vessel 12 would measure approximately 7 inches by 3.5 inches and the vessel-body 20, 7 inches in height. Discharge nozzle 24 would extend 5–7 inches beyond the vessel-body 20. These dimensions would suffice for the average adult. Larger or smaller versions would follow the same general proportional relationships.

Operation—FIGS. 1A–1I

The User Powered Personal Hygiene Apparatus operates, by filling the tapering vessel body 20 with desired fluid through the filling point cap connection 18 located at the base of vessel 12. Other embodiments can accomplish filling from the detachable nozzle tip connection 28 by removing the detachable nozzle tip 26, as in FIGS. 1B, 1C, 1D, 1E, 1F, 1G and 1H, as well as from the filling-point-cap-connection 18 that is also provided. The embodiments that incorporate a vessel-with-a-connection-for-a-discharge-neck 21 to be attached, FIGS. 1F, 1G, 1H, can be filled from this point as well as from either the detachable-nozzle-tip-connection 28 or from the filling-point-cap-connection 18. Vessels that do not provide a base-of-vessel-filling-point-cap 14 must be filled by either the detachable-nozzle-tip-connection 28 or at the connection for the discharge-neck 21. Vessels with a molded-to-vessel-discharge-neck 22 must have a filling-point-cap-connection or a detachable-nozzle-tip-connection 28 if a filling-point-cap-connection 18 is not provided.

Once the vessel is filled and the user is seated on the toilet the apparatus is inverted so that the vessel-discharge-neck 22 is pointing downward. The discharge-neck 22 is inserted between the users legs so that the nozzle-tip extends about four to seven inches below the top of the toilet seat and extends into the toilet bowl space in front of the user and aligned so that the tapering-vessel-body 26 is perpendicular to the plane of the toilet seat. See FIG. 6A. The User Powered Personal Hygiene Apparatus (UPPHA) will rest comfortably in this position with the tapering-vessel-body 20 resting on the inner thighs of the user, and the discharge-nozzle 24 visible directly below. The user then grasps the vessel body with both hands, thumbs in front and the fingers extending around from the sides. The user then pushes the tapering-vessel-body 20 forward pivoting the UPPHA at the axis-of-rotation 55 (FIG. 6A) so that the nozzle-tip 24 is moved backward and rotates upward toward the anus. The upward angle of the discharge-nozzle 24 and the discharge hole(s) 25 and the geometry of the UPPHA work together so that when pivoted, they rotate and position the discharge hole(s) directly beneath the anus. The user then compresses the sides of the tapering-vessel-body 20 and fluid is vigorously expelled through precise discharge hole(s) 25 in the nozzle-tip 24 onto the anus. The user can apply to specific areas by small movements of the pivot point(not-shown) to position the tip where application is desired. Fluid pressure and discharge volume is regulated by how hard the user squeezes, and which size discharge hole(s) 25 are used. Since all the fluid is not expelled with one compression air must re-enter the tapering-vessel-body 20 and re-expand the vessel 20. By letting up on the pressure being applied to the tapering-vessel-body 20, tapering vessel body 20 begins to return to its original shape and will suck air in through the nozzle-discharge hole(s) 25, however, this is slow and runs the risk of having fecal matter sucked into the vessel from the run-off if the discharge nozzle is not moved away from the anus quickly while the vessel is re-expanding. Since allowing the nozzle hole(s) to act as an air return pathway is not always desired, the UPPHA is available with an air-valve 16 that the user may open to allow the quick re-introduction of air and re-expansion of the vessel-body 20 and then when the air-valve is closed, and the vessel-body 20 has re-expanded, the user now has a large volume to compress for another vigorous fluid discharge.

By pulling the vessel-body 20 back toward the user's body the nozzle-tip 24 and discharge hole(s) 25 are pivoted and rotated away from the anus and the UPPHA will rest comfortably between the thighs and allow the user to remove loosened debris before another application of fluid. Or, the user may place the UPPHA back upright on the counter or floor. Toilet paper may be used in conjunction with cleansing fluids to facilitate and ensure that cleansing was completely accomplished. Used properly the UPPHA should reduce toilet paper usage 75%. Anal cleansing is accomplished by the pressurized application of the fluids being expelled from the UPPHA and applied on the anal regions. Mild soaps or cleansing solutions, vinegar, teas, baking soda etc. may be introduced when filling the UPPHA to accomplish superior cleansing action when applied to the anus as this will help dissolve sticky fecal matter. A second UPPHA should be ready if soaps are added to the wash water. The second UPPHA should be filled with clean water to rinse the rectal area after a soapy wash so no irritation occurs. Pat dry with toilet paper.

The UPPHA should be kept clean and may be washed with hot soapy water, rinsed and allowed to dry. It is unbreakable and may be stored on a counter for ready use.

FIG. 1H is an embodiment that does not incorporate a base-of-vessel-filling-cap 14 or an air-valve. A UPPHA without these features is used in the same way as vessels having these features except that after compressing vessel-body 20 air can enter vessel body 20 only through the discharge-hole(s) and must be filled at the discharge-neck-connection 32 or from a detachable nozzle-tip connection 28.

UPPHA's that do not have the molded-in-place-discharge-nozzles 24 may be completely sealed for travel in a filled condition utilizing a vessel-sealing-cap-for-travel 46 or a detachable nozzle-tip 26 that has no discharge-holes (not shown) or an appropriate sealing-cap (not shown).

Essentially, the embodiments described in FIGS. 1A to 1I all share the same basic geometry and features that allow the UPPHA as a whole to achieve its purpose. FIGS. 1D and 1E have a kidney-shaped-base 38 and a kidney-shaped-vessel 40. This embodiment allows a little extra space for male users and a more comfortable griping surface.

Besides being ergonomic the shape of the vessel-body 20 in all described embodiments adds to the function of the whole by allowing for a large surface area in the area where the vessel is compressed and allows a maximum deflection of the vessel-body 20 resulting in higher pressure and volume for a longer period of time. The apparatus is also stable and not prone to falling over, especially when filled, due to the large base area.

Conclusion, Ramifications, and Scope of Invention

Thus the reader will see that the UPPHA with its unique geometry and pivot into position structure provides an aesthetic, efficient, convenient, portable, ergonomic, easy to use, durable, and economical means for achieving superior personal cleansing of the anus and genital area.

While my above description contains many specifics, these should not be construed as limitations on the scope of the invention, but rather as an exemplification of one preferred embodiment thereof. Many other variations are possible. For example, instead of a triangular vessel-body one could have a cylindrical vessel, however, this would not fit the anatomy of a person sitting on the toilet as well, and it would be clumsy and awkward to handle and prone to falling over. One could incorporate a semi-flexible discharge-neck that would hold its shape when bent into position. One could have an accordion-like-vessel that would continue collapsing when squeezed and not need any means of re-expansion. Accordingly, the scope of the invention should be determined not by the embodiment(s) illustrated, but by the appended claims and their legal equivalents.

What is claimed is:

1. A user-powered, hand-held, personal hygiene apparatus comprising:
    a fluid containing vessel having a neck extending from proximate one end of the vessel and terminating in a fluid discharge nozzle with an open channel therethrough, the vessel having a resiliently compressible wall with an oval-shaped transverse cross section providing opposed large surface areas which can be grasped between a user's thumbs and fingers to enable the user to manually urge fluid out of the vessel through the nozzle while regulating the pressure and volume of the discharged fluid by compressing the opposed areas of the wall between the thumbs and fingers, the neck of the vessel further extending laterally of the vessel to position the nozzle laterally beyond a side of the vessel and being formed for discharge of fluid from the vessel in an upward direction when the vessel is inverted in a near vertical position and supported on the user's thighs; and
    a fill aperture and closure therefor provided on the vessel proximate an end of the vessel opposite the neck on the same side of the vessel from which the neck laterally extends, the fill aperture positioned to facilitate filling of the vessel while in a substantially horizontal orientation without discharge of fluid through the open channel of the nozzle.

2. The personal hygiene apparatus as defined in claim 1 wherein,
    the neck is arcuate and curves laterally from a longitudinal axis of the vessel by greater than 90°.

3. The personal hygiene apparatus as defined in claim 1 wherein,
    the vessel has a planar end wall for support of the vessel on a horizontal surface with a longitudinal axis of the vessel in a vertical orientation.

4. A user-powered, hand-held, personal hygiene apparatus comprising:
    a fluid containing vessel having a neck extending from proximate one end of the vessel and terminating in a fluid discharge nozzle with an open channel therethrough, the vessel having a resiliently compressible wall and an oval cross section configured to facilitate grasping by a user between the thumbs and fingers of the user to manually regulate the pressure and volume of fluid forceably discharged out of the vessel through the nozzle by compressing opposed portions of the wall, and the neck of the vessel extending laterally of the vessel to a position laterally beyond a side of the vessel;
    a fill aperture and closure therefor provided on the vessel proximate an end of the vessel opposite the neck, the fill aperture being further positioned in a side wall of the vessel spaced toward the neck from an end wall of the vessel, the fill aperture position facilitating filling of the vessel while in a substantially horizontal orientation without discharge of fluid through the open channel of the nozzle.

5. The personal hygiene apparatus as defined in claim 4 wherein,
    the end wall opposite the neck is planar and formed for support of the vessel in a vertical orientation on a horizontal support surface.

6. The personal hygiene apparatus as in claim 5 wherein,
    a side wall opposite the side wall having the fill aperture therein is substantially planar for stable support of the vessel in a horizontal orientation on a horizontal surface while filling.

7. The personal hygiene apparatus as defined in claim 4 wherein,
    the vessel has a central longitudinal axis and the neck extends laterally of the longitudinal axis vessel and in a rearward direction for discharge of fluid from the nozzle in an upward direction when the vessel is inverted with the neck depending downward.

8. A user-powered, hand-held, personal hygiene apparatus comprising:
    a fluid containing vessel having a neck proximate a neck end of the vessel with the neck terminating in a fluid discharge channel, the vessel having a manually graspable oval-shaped transverse cross section with opposed resiliently compressible wall portions of large area enabling a user to manually urge fluid out of the vessel through the channel by squeezing the grasped wall portions toward each other, and the neck of the vessel extending laterally of the vessel to a position laterally beyond a side of the vessel;
    a fill aperture and closure therefore provided on the vessel proximate and spaced from an end of the vessel opposite the neck end; and
    the vessel further having a configuration suitable for stable support of the vessel on a planar area of both of: (a) a side wall of the vessel during filling, and (b) on the end wall of the vessel opposite the neck end.

9. The personal hygiene apparatus as defined in claim 8 wherein,
    the neck is formed to orient the nozzle for discharge of fluid in an upward direction when the vessel is vertically oriented with the neck depending downwardly therefrom.

* * * * *